(12) United States Patent
Loertscher et al.

(10) Patent No.: US 10,167,559 B2
(45) Date of Patent: Jan. 1, 2019

(54) NEGATIVE PATTERNING APPROACH FOR ULTRA-NARROW GAP DEVICES

(71) Applicants: International Business Machines Corporation, Armonk, NY (US); University of Basel, Basel (CH)

(72) Inventors: Emanuel Loertscher, Bonstetten (CH); Marcel Mayor, Basel (CH); Gabriel Fernando Puebla Hellman, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 150 days.

(21) Appl. No.: 15/249,916

(22) Filed: Aug. 29, 2016

(65) Prior Publication Data

US 2018/0057930 A1    Mar. 1, 2018

(51) Int. Cl.
| | |
|---|---|
| *G03F 7/00* | (2006.01) |
| *C23C 16/56* | (2006.01) |
| *G01N 21/552* | (2014.01) |
| *C23C 16/44* | (2006.01) |
| *C23C 16/04* | (2006.01) |
| *G03F 7/20* | (2006.01) |
| *C23C 14/04* | (2006.01) |
| *G03F 7/40* | (2006.01) |
| *B05D 1/32* | (2006.01) |

(52) U.S. Cl.
CPC .............. *C23C 16/56* (2013.01); *C23C 16/04* (2013.01); *C23C 16/44* (2013.01); *G01N 21/554* (2013.01); *B05D 1/32* (2013.01); *C23C 14/04* (2013.01); *C23C 14/042* (2013.01); *G03F 7/0002* (2013.01); *G03F 7/2059* (2013.01); *G03F 7/40* (2013.01)

(58) Field of Classification Search
CPC ....... C23C 16/042; C23C 16/44; C23C 16/56; C23C 14/04; C23C 14/042; G03F 7/0002; G03F 7/2059; G03F 7/40; B05D 1/32
USPC .................................................. 427/98.4, 282
See application file for complete search history.

(56) References Cited

U.S. PATENT DOCUMENTS

| | | | | |
|---|---|---|---|---|
| 5,244,538 A | * | 9/1993 | Kumar | ............... H05K 3/045 216/18 |
| 9,240,346 B2 | | 1/2016 | Lee et al. | |
| 2006/0134889 A1 | * | 6/2006 | Sadra | ............... H01L 21/26586 438/473 |
| 2010/0003789 A1 | * | 1/2010 | Caplet | ............... B81C 1/00285 438/124 |

(Continued)

FOREIGN PATENT DOCUMENTS

| | | |
|---|---|---|
| CN | 1716073 A | 1/2006 |
| CN | 100430810 C | 11/2008 |

(Continued)

OTHER PUBLICATIONS

English translation for Japan Application No. JP2015206949A.
English translation for China Application No. CN104298011A.
English translation for China Application No. CN103226265A.

(Continued)

*Primary Examiner* — Brian K Talbot
(74) *Attorney, Agent, or Firm* — Vazken Alexanian; Ryan, Mason & Lewis, LLP (57) ABSTRACT

A method for manufacturing a gap device includes forming a template structure on a substrate, depositing an active material layer on the substrate and on the template structure, wherein the active material layer covers at least top and side surfaces of the template structure, planarizing the active material layer, and selectively removing the template structure with respect to the active material layer and the substrate.

16 Claims, 10 Drawing Sheets

(56) References Cited

U.S. PATENT DOCUMENTS

2014/0358128 A1  12/2014  Montazeri et al.
2016/0118249 A1  4/2016  Sreenivasan et al.

FOREIGN PATENT DOCUMENTS

| CN | 103226265 A | 7/2013 |
| CN | 104298011 A | 1/2015 |
| JP | 2015206949 A | 11/2015 |
| KR | 100475636 B1 | 2/2005 |
| WO | 2016065308 A1 | 4/2016 |

OTHER PUBLICATIONS

English translation for China Application No. CN100430810C.
English translation for China Application No. CN1716073A.
English translation for Korea Application No. KR100475636B1.
Alexandre G. Brolo, "Plasmonics for Future Biosensors," Nature Photonics, Nov. 2012, pp. 709-713, vol. 6.
C.C. Neacsu et al., "Scanning-Probe Raman Spectroscopy with Single-Molecule Sensitivity," Physical Review B, May 2006, pp. 193406-1-193406-4, vol. 73, No. 19.
Wikipedia, "Plasmonic Metamaterial," https//en.wikipedia.org/w/index.php?title=Plasmonic_metamaterial&printable=yes, May 27, 2016, 6 pages.
C. Haffner et al., "All-Plasmonic Mach-Zehnder Modulator Enabling Optical High-Speed Communication at the Microscale," Nature Photonics, Jul. 17, 2015, pp. 525-528, vol. 9.
A.N. Grigorenko et al., "Graphene Plasmonics," Nature Photonics, Nov. 5, 2012, pp. 749-758, vol. 6.

* cited by examiner

FOR EASE OF EXPLANATION, ELEMENTS 104 & 204 ARE NOT SHOWN IN FIG. 6D

FOR EASE OF EXPLANATION, ELEMENT 104 IS NOT SHOWN IN FIGS. 8C & 8D

FOR EASE OF EXPLANATION, ELEMENT 104 IS NOT SHOWN IN FIGS. 9C AND 9D

FOR EASE OF EXPLANATION, ELEMENT 104 IS NOT SHOWN IN FIG. 10C & 10D

NEGATIVE PATTERNING APPROACH FOR ULTRA-NARROW GAP DEVICES

BACKGROUND

The interaction of light and a conductor leads to collective oscillations of mobile/free charge carriers of the conductor under an incident electromagnetic field. Theses collective oscillations of electrons in a medium with mobile/free charge carriers are referred to as surface plasmon polaritons (SPP), or plasmons. The oscillations together with the induced charge-distribution generate a near-field effect that enables light to be concentrated below the diffraction limit and guided along a dielectric-conductor interface at optical subwavelengths and at frequencies in the hundreds of terahertz (THz).

Plasmon-based devices (also referred to herein as "plasmonic devices") provide an opportunity to merge optics and electronics at subwavelength dimensions, offering the potential of integrating optical components with dimensions much closer to state-of-the-art electronic devices than photonic building blocks. When compared with photonic building blocks, plasmon-based devices enable increased bandwidth for short- and long-range communication, electro-optical or all-optical switching, and can significantly reduce cost and complexity due to the monolithic integration of electronic and optical components. Plasmonic structures also enable the concentration and confinement of optical fields to $nm^3$ sized volumes. This allows for increased interaction between the optical field and optically active materials in a volume, enabling spectroscopy of analytes at sensitivities approaching the single-molecule level. Robust devices for detecting chemicals at this sensitivity level allow for a large range of applications, ranging from quality control in health and medical fields, to security and environmental monitoring.

While being important to applications of plasmonics, and providing beneficial near-field effects, the small size of plasmonic devices and the need for their close arrangement poses challenges for the implementation and application of such structures. Although bottom-up techniques based on nanoparticles or nano-rods can be utilized for the fabrication of sensing elements, tight size tolerances, missing methods for accurate placement on true nanometer accuracy levels, and non-tailorable dimensions to match resonant conditions, limit the usefulness of these bottom-up techniques, even for simple device geometries. Advances in top-down lithography have enabled the direct pattering of such structures to the extent that the limiting factors are now line-edge roughness (caused by pattern transfer) and material intrinsic inhomogeneity in the morphology, such as, for example, grain boundaries and domains.

Non-ideal geometries, high line-edge roughnesses and heterogeneous morphologies can lead to considerable losses, severely limiting the application range of plasmonic devices. Standard methods to increase, for example, grain size, do not lend themselves easily to the fabrication flow, as they cause significant surface roughness, which is a source of loss in itself. While enhancing the material and patterning properties of resulting devices is an important issue, a further challenge is the alignment of structures, for example, channels to the feedgap of a nanoplasmonic devices, requiring nanometer or even sub-nanometer tolerances.

SUMMARY

According to an exemplary embodiment of the present invention, a method for manufacturing a gap device includes forming a template structure on a substrate, depositing an active material layer on the substrate and on the template structure, wherein the active material layer covers at least top and side surfaces of the template structure, planarizing the active material layer, and selectively removing the template structure with respect to the active material layer and the substrate.

According to an exemplary embodiment of the present invention, a method for manufacturing a gap device includes forming a template structure on a substrate, patterning the template structure to a critical dimension, removing a portion of the template structure to reduce the template structure to a second dimension less than the critical dimension, depositing an active material layer on the substrate and on the reduced template structure, wherein the active material layer covers at least a portion of side surfaces of the reduced template structure, removing excess portions of the active material layer, and selectively removing the reduced template structure with respect to the active material layer.

According to an exemplary embodiment of the present invention, a method for manufacturing a gap device includes forming a template structure on a substrate, reducing the template structure to a width less than about 10 nanometers, depositing an active material layer on the substrate and at least on top and side surfaces of the template structure, removing excess portions of the active material layer to expose the top surface of the template structure, and selectively removing the template structure with respect to the active material layer and the substrate to create a gap in the active material layer corresponding to the width of the template structure.

These and other exemplary embodiments of the invention will be described in or become apparent from the following detailed description of exemplary embodiments, which is to be read in connection with the accompanying drawings.

BRIEF DESCRIPTION OF THE DRAWINGS

Exemplary embodiments of the present invention will be described below in more detail, with reference to the accompanying drawings, of which:

FIGS. 6A and 6B are cross-sectional views, FIG. 6C is a top view.

FIGS. 7A and 7B are cross-sectional views, FIG. 7C is a top view.

FIGS. 8A and 8B are cross-sectional views, FIG. 8C is a top view.

FIGS. 9A and 9B are cross-sectional views, FIG. 9C is a top view.

FIGS. 10A and 10 B are cross-sectional views, FIG. 10C is a top view.

DETAILED DESCRIPTION

Exemplary embodiments of the invention will now be discussed in further detail with regard to gap devices and methods of manufacturing same and, in particular, to the fabrication of ultra-narrow gap optical structures using a buried template that has a reduced dimension.

It is to be understood that the various layers and/or regions shown in the accompanying drawings are not drawn to scale, and that one or more layers and/or regions of a type commonly used in, for example, plasmon-based devices and/or other ultra-narrow gap devices may not be explicitly shown in a given drawing. This does not imply that the layers and/or regions not explicitly shown are omitted from the actual devices. In addition, certain elements may be left out of particular views for the sake of clarity and/or simplicity when explanations are not necessarily focused on the omitted elements. Moreover, the same or similar reference numbers used throughout the drawings are used to denote the same or similar features, elements, or structures, and thus, a detailed explanation of the same or similar features, elements, or structures will not be repeated for each of the drawings.

The devices and methods for forming same in accordance with embodiments of the present invention can be employed in applications, hardware, and/or electronic systems. Suitable hardware and systems for implementing embodiments of the invention may include, but are not limited to, personal computers and other computing devices, sensing devices, waveguides, modulators, communication networks, electronic commerce systems, portable communications devices (e.g., cell and smart phones), solid-state media storage devices, functional circuitry, etc. Systems and hardware incorporating the devices are contemplated embodiments of the invention. Given the teachings of embodiments of the invention provided herein, one of ordinary skill in the art will be able to contemplate other implementations and applications of embodiments of the invention.

The embodiments of the present invention can be used in connection with semiconductor or non-semiconductor devices that may require, for example, plasmonic devices and/or other ultra-narrow gap devices. By way of non-limiting example, the semiconductor and non-semiconductor devices can include, but are not limited to plasmonic devices and/or other ultra-narrow gap devices, and/or semiconductor and non-semiconductor devices that use plasmon-based and/or other ultra-narrow gap technology.

Besides plasmonic devices, other field-enhancing systems such as conductive oxides can be patterned using embodiments of the present invention. Fabricating small gaps between two materials, in accordance with embodiments of the present invention, can be applied, for example, to transistor technology and/or in nanoscale materials, such as two-dimensional (2D) layered materials.

As used herein, "height" refers to a vertical size of an element (e.g., a layer, trench, hole, etc.) in the cross-sectional views measured from a bottom surface to a top surface of the element, and/or measured with respect to a surface on which the element is directly on. Conversely, a "depth" refers to a vertical size of an element (e.g., a layer, trench, hole, etc.) in the cross-sectional views measured from a top surface to a bottom surface of the element.

As used herein, "lateral," "lateral side," "lateral surface" refers to a side surface of an element (e.g., a layer, opening, etc.), such as a left or right side surface in the drawings.

As used herein, "width" or "length" refers to a size of an element (e.g., a layer, trench, hole, etc.) in the drawings measured from a side surface to an opposite surface of the element.

As used herein, terms such as "upper", "lower", "right", "left", "vertical", "horizontal", "top", "bottom", and derivatives thereof shall relate to the disclosed structures and methods, as oriented in the drawing figures. For example, as used herein, "vertical" refers to a direction perpendicular to a substrate in the cross-sectional views, and "horizontal" refers to a direction parallel to a substrate in the cross-sectional views.

As used herein, unless otherwise specified, terms such as "on", "overlying", "atop", "on top", "positioned on" or "positioned atop" mean that a first element is present on a second element, wherein intervening elements may be present between the first element and the second element. As used herein, unless otherwise specified, the term "directly" used in connection with the terms on", "overlying", "atop", "on top", "positioned on" or "positioned atop" or the term "direct contact" mean that a first element and a second element are connected without any intervening elements, such as, for example, intermediary conducting, insulating or semiconductor layers, present between the first element and the second element.

As used herein, a "gap device" or "ultra-narrow gap device" refers to a device that is semiconductor-fabrication based, for example, having a semiconductor platform or a semiconductor active structure, and can include functional components which are non-semiconductor and/or semiconductor-based. Alternatively, a gap device or ultra-narrow gap device includes non-semiconductor components, and is not semiconductor-based, for example a transparent glass substrate. Gap devices or ultra-narrow gap devices can include, but are not necessarily limited to, optical field-enhancement devices, plasmonic field-enhancement devices, plasmonic sensing devices, optical circuits, electro-optical circuits, electrical circuits, electro-optical modulators, electronic devices, molecular-based devices, tunneling devices, non-linear optic devices, and field-emission devices. In most of these devices, an ultra-narrow gap carries the main functionality and gap dimensions below 10 nm are favorable in terms of integration, performance and stability aspects.

In accordance with an embodiment of the present invention, ultra-narrow gap plasmonic structures are fabricated using an inverse patterning approach (also referred to herein as "pattern-first approach" or "negative template approach"). Embodiments of the present invention allow a number of active-material post-growth or post-deposition treatment steps, such as annealing, yielding vertical sidewalls with low line-edge roughness, as well as low roughness of both top and side surfaces of a metal film or improved morphologies. Additionally, processing in accordance with embodiments of the present invention, allows for self-alignment of feeding- and analyte-guiding structures as well as fabrication of electrical, electro-optical, all-plasmonic, all-optical and photonic devices. The disclosed patterning approaches can be generic for any type of ultra-narrow gap device.

Embodiments of the present invention enable the fabrication of low roughness, feedgap based plasmonic structures. For example, by patterning a gap in a sacrificial silicon layer, the complement of a feedgap can be fabricated using the highly developed processes available for silicon, yielding structures with vertical sidewalls and low line-edge roughness. These structures can further be reduced in size using approaches such as, but not necessarily limited to, cycled oxidation and oxide removal, allowing for extremely precise control over dimensions. By depositing an active material layer in a subsequent step, methods such as, but not necessarily limited to, epitaxial deposition or bottom-up seed-mediated growth, may be applied to obtain materials with the desired properties and allowing for post-growth treatment procedures, such as, but not necessarily limited to, annealing and recrystallization. Chemical mechanical polishing (CMP) or mechanical polishing are employed to remove the excess metal on top of a resulting gap structure, significantly decreasing the top-surface roughness of the active layer. In a further step, a buried template is selectively removed, using, for example, etching, leading to the desired geometry with unprecedented active-material quality regarding gap sizes, surface roughness and morphology achieved by using the buried template structure as a spacer element throughout all relevant process steps including post-growth and post-deposition treatments.

By covering a structure with oxide and patterning openings before etching the silicon, buried channels leading perfectly through the feed gaps of plasmonic structures can be obtained as the active layer and the channel are self-aligned in respect to each other. As a result, embodiments of the present invention allow for advanced sensing devices, employing high field enhancements of resonant plasmonic structures to be employed for sensing down to the single-molecule level owing to active analyte guiding. Furthermore, embodiments of the present invention allow for the fabrication of low-loss plasmonic and photonic devices by inverse patterning of active structures, such as, for example, waveguides, modulators etc., which are suitable for direct and quasi-monolithic co-integration of miniaturized plasmonic and photonic devices with conventional semiconductor electronics for computing or silicon photonics for long-range transmission.

In accordance with an embodiment of the present invention, a negative-patterning fabrication procedure is disclosed, which combines cycled etching, molding overgrowth and removal of excess material and buried material such that: (i) a sacrificial complement of a desired structure (referred to herein as a "buried template") is patterned first; (ii) the feature size of the buried template can further be reduced down to smaller (e.g., nanometer) dimensions by selective etching; (iii) on top of the buried template, a second material (referred to herein as "active material") is deposited using a deposition technique such that the active material conformally covers an interface to the buried template; (iv) a planarization process (e.g., CMP) is employed to remove excess active material (e.g., overburden) to form separated structures of the active material; (v) the buried template can be selectively removed with a desired pattern shape remaining in the active material as previously defined by the patterned and reduced buried template.

Figure 1:
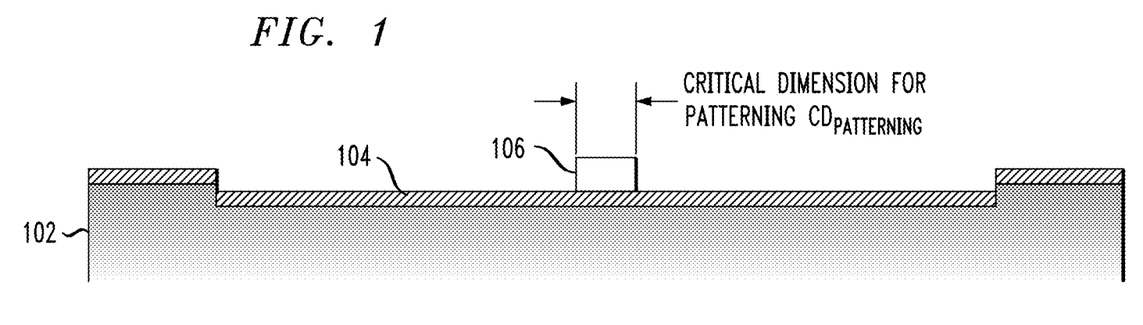
FIG. 1 is a cross-sectional view illustrating fabrication of a gap device and showing patterning of a buried template, according to an exemplary embodiment of the present invention.

FIG. 1 is a cross-sectional view illustrating fabrication of a gap device and showing patterning of a buried template, according to an exemplary embodiment of the present invention. Referring to FIG. 1, a dielectric layer 104 formed of a material that can remain during subsequent selective removal of a buried template is formed on a substrate 102. The substrate 102 can be a semiconductor substrate including, but not necessarily limited to, Si, SiGe, SiC, SiGeC or other like semiconductor. In addition, multiple layers of the semiconductor materials can be used as the semiconductor material of the substrate 102. Alternatively, the substrate 102 can also be a dielectric, such as, for example, glass (e.g., quartz glass) or sapphire, and can include the same material as the dielectric 104.

In accordance with an embodiment of the present invention, a template structure 106 (also referred to herein as a "buried template") is formed on the dielectric layer 104. Forming the template structure can be performed by depositing a layer and patterning the layer into the template structure 106. Alternatively, the template structure 106 can be deposited directly, without a need to perform patterning. The latter direct deposition process can be performed, for example, in connection with carbon nanotubes, nanowires, nanocrystals. Top-down assisted deposition of such template structures can be assisted by micro- and nanofluidics and may include furthermore bottom-up assembly techniques such as self-assembly of template structures or assembly techniques based on molecular recognition.

When deposition and patterning are performed, deposition of a material layer that will form the template structure can be performed using deposition techniques, such as, for example, chemical vapor deposition (CVD), plasma enhanced CVD (PECVD), physical vapor deposition (PVD), atomic layer deposition (ALD), molecular beam deposition (MBD), pulsed laser deposition (PLD), and/or liquid source misted chemical deposition (LSMCD). Methods for patterning can include, for example, photolithography (PL), electron-beam lithography (EBL), probe-based lithography, nanoimprint lithography, yielding critical dimensions ($CD_{patterning}$) between about 1 µm-about 2 µm for PL, about 10 nm-about 100 nm for EBL and 1-50 nm for probe-based lithography for the width of the buried template 106. In accordance with embodiments of the present invention, the material of the template structure 106 can include, but is not necessarily limited to, metallic materials, semiconducting materials, such as silicon (Si), poly-Si, amorphous-Si, or III-V compound semiconductors, dielectrics or organic (carbon-based) materials.

Figure 2:
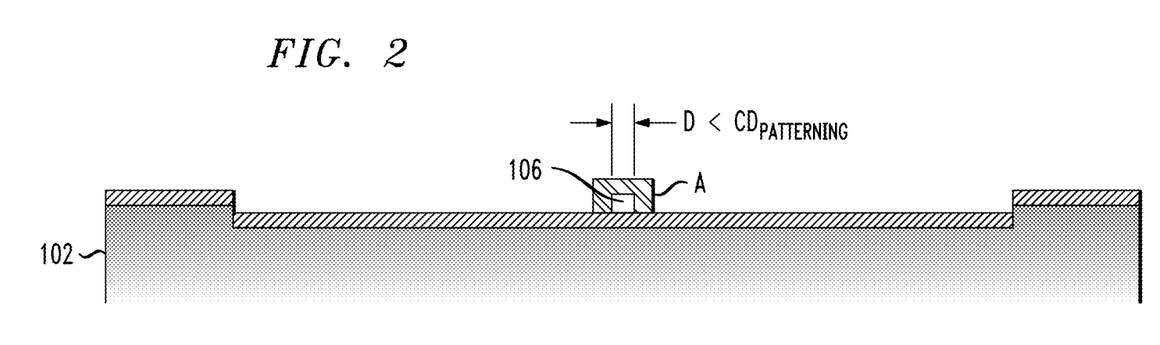
FIG. 2 is a cross-sectional view illustrating fabrication of a gap device and showing reducing of the dimensions of the buried template, according to an exemplary embodiment of the present invention.

FIG. 2 is a cross-sectional view illustrating fabrication of a gap device and showing reducing of the dimensions of the buried template, according to an exemplary embodiment of the present invention. Referring to FIG. 2, according to an embodiment of the present invention, further reduction of the width of the buried template below the critical dimension of the patterning ($CD_{patterning}$) can be achieved, for example, by oxidation and/or etching. The etching mechanism can be self-limiting and/or cycleable to improve control over dimensions, so that the width (D) is reduced to less than about 10 nm. As can be seen in FIG. 2, the portion marked "A" represents the template structure prior to the reduction having the critical dimension of the patterning ($CD_{patterning}$). In addition, treatment steps, such as, for example, annealing steps, can be performed to reduce line-edge and surface roughness of the buried template 106. For example, a hydrogen anneal can be performed smoothening the surface of the template structure 106. According to an embodiment, the step of reducing the dimensions of the buried template can be omitted if the deposited and/or patterned template structure 106 is already at a desired width for further processing. Although one template structure 106 is shown, it is to be understood that multiple template structures 106 spaced apart from each other can be formed on the dielectric layer 104 subject to design constraints. In the third dimension (not shown in the cross-sectional view), by way of non-limiting example, the template structure 106 can be patterned as shown in FIGS. 6D and 8D discussed further herein, or have other configurations.

Figure 3:
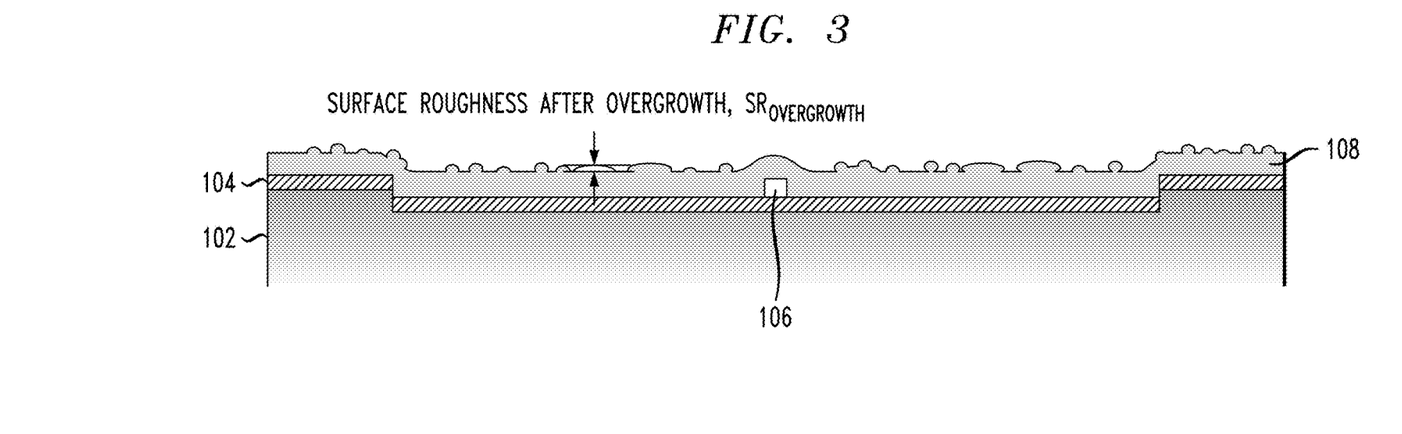
FIG. 3 is a cross-sectional view illustrating fabrication of a gap device and showing active material deposition, according to an exemplary embodiment of the present invention.

FIG. 3 is a cross-sectional view illustrating fabrication of a gap device and showing active material deposition, according to an exemplary embodiment of the present invention. Referring to FIG. 3, an active material 108, such as, for example, an electrically conductive metal such as gold (Au), a monocrystalline material such as Au nanoplatelets, a 2D-layered material such as graphene, can be deposited over the template structure 106 using, for example, PVD, such as electron-beam deposition, sputtering, and/or molecular beam epitaxy, ALD, spin-coating, electro-driven or electro-less plating, bottom-up growth, such as seed-mediated growth, printing and other transfer approaches (for 2D-layered materials with post annealing), deposition from solution, and/or CVD. As can be seen in FIG. 3, the active layer 108 covers top and side surfaces of the template structure 106 and is formed on exposed portions of the dielectric layer 104. An upper surface of the active layer 108 is not planar, and includes a surface roughness, which is depicted as $SR_{Overgrowth}$ in FIG. 3, which can vary at portions along the upper surface of the active layer 108 depending on a height of a malformation of the surface.

The active material layer 108 on opposing sides of the template structure 106 can be treated to improve surface roughness and material morphology of the active material and/or interfacial quality between the active material layer 108 and the template structure 106. Treatment can include, for example, annealing, activation, conditioning, and formation to result in strain-release, removal of voids, optimization of grain and domain sizes, removal of additives, and/or recrystallization. Such treatments can be performed regardless of their effect on the surface of the active material layer 108 because, as explained further herein, the top-surface of the active material layer 108 is planarized in a subsequent step, and the buried template structure 106 functions as a separating spacer between opposing sections of the active material layer 108 after planarization.

Figure 4:
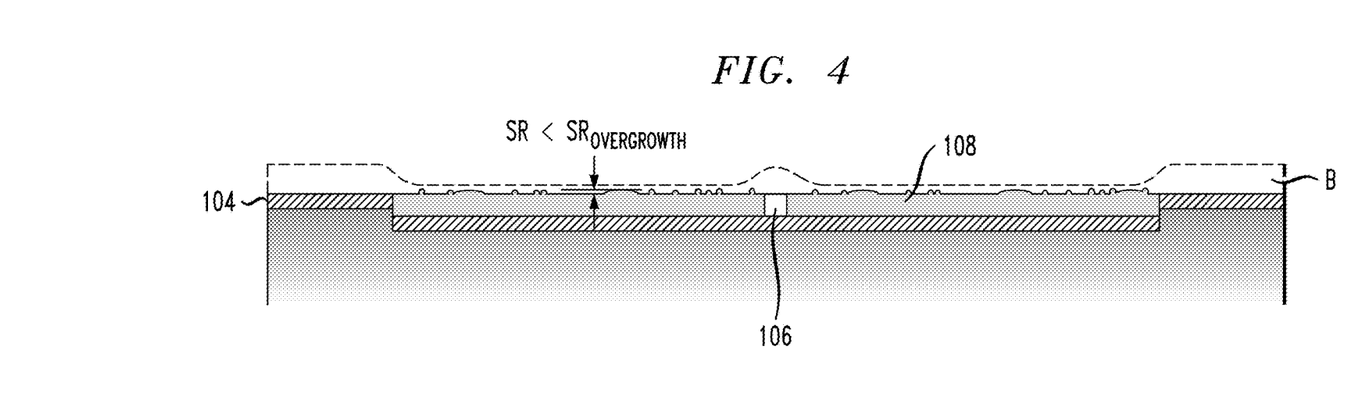
FIG. 4 is a cross-sectional view illustrating fabrication of a gap device and showing removal of excess active material, according to an exemplary embodiment of the present invention.

FIG. 4 is a cross-sectional view illustrating fabrication of a gap device and showing removal of excess active material, according to an exemplary embodiment of the present invention. In accordance with an embodiment of the present invention, chemical-mechanical polishing (CMP), mechanical polishing, etching, or other planarization process is performed to remove excess active material. The height of the removed active material B is outlined by a dotted line in FIG. 4. The removal process removes portions of the active material layer 108 (e.g., the overburden on top of the template structure) down to or slightly below the top surface of the template structure. As used herein, "slightly below" refers to the height of the template structure and the accuracy of the removal process' stopping conditions combined with the respective process tolerances. In practice, the CMP, for example, is stopped slightly after reaching the top surface to ensure complete separation of the two segments of the active material.

As can be seen in FIG. 4, the planarizing separates the active material layer 108 into a first portion on a first side (e.g., left side) of the template structure 106, and a second portion on a second side (e.g., right side) of the template structure 106 opposite the first side. In the third dimension (not shown in the cross-sectional view), there can be additional arbitrary separations created by the planarization step and depending on the design of the template structure. The planarization process reduces a surface roughness of the active material layer 108 by decreasing a height of or eliminating malformations on an upper surface of the active material layer 108. As can be seen, a surface roughness (SR) after the planarization is less than a surface roughness ($SR_{Overgrowth}$) after formation of the active material layer 108.

Figure 5:
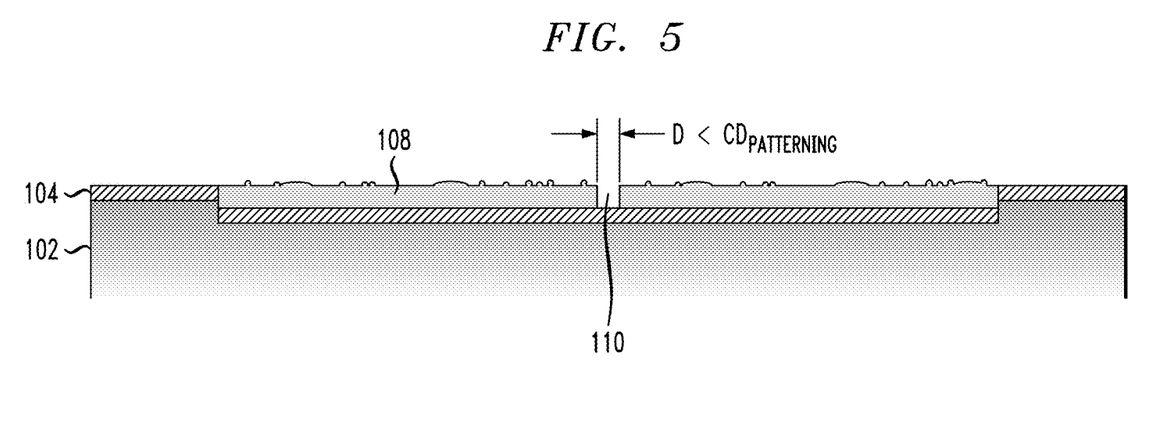
FIG. 5 is a cross-sectional view illustrating fabrication of a gap device and showing selective removal of the buried template, according to an exemplary embodiment of the present invention.

FIG. 5 is a cross-sectional view illustrating fabrication of a gap device and showing selective removal of the buried template structure, according to an exemplary embodiment of the present invention. Referring to FIG. 5, after planarization, the template structure 106 is selectively removed using, for example, an etching process, such as isotropic etching, including wet etching and/or gas etching depending on the material used for the template structure 106. For example, in the case of Si-composed buried templates xenon difluoride ($XeF_2$) can be used as an etchant. In case of metal-composed buried templates, wet-chemical etchants can be used. In case of organic buried templates, reactive ion etching (RIE) can be used. As shown in FIG. 5, a gap 110 corresponding to the dimension D of the template structure 106, is formed between opposing sections of the active material layer 108 in the space previously occupied by the template structure 106.

The process described in connection with FIGS. 1-5 can be used for aligning gas and liquid channels to electrical, optical and plasmonic structures, acting, for example, as sensing devices. In this case, the process described in connection with FIGS. 1-5 is used to create self-aligned channels between nano-antennas. For that purpose, a material overgrowth (e.g., dielectric) of the entire structure is required between the steps described in connection with FIGS. 4 and 5 (see FIGS. 6A, 6B, 6C and 6D), followed by a channel opening step by fabricating opening in the topmost layer and the removal of the buried template 106 through the openings and the channels (FIGS. 7A, 7B, 7C and 7D).

Figure 6A:
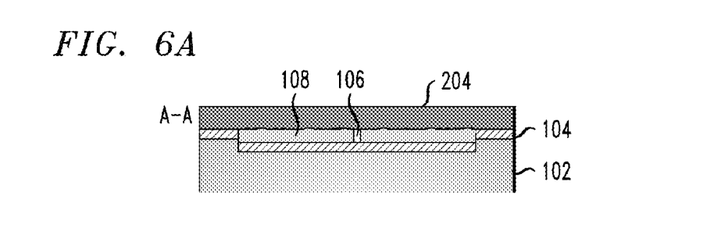
Figure 6B:
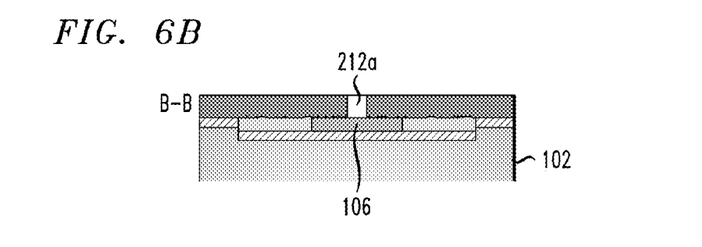
Figure 6C:
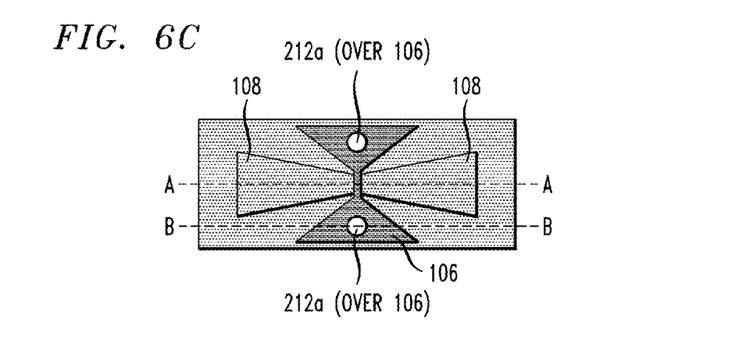
Figure 6D:
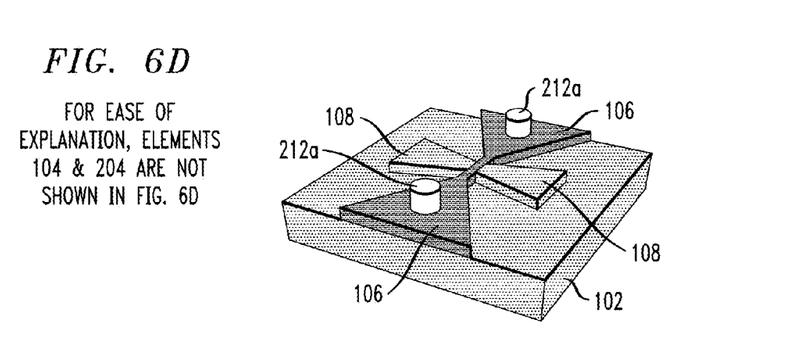
FIG. 6D is a three-dimensional view illustrating fabrication of a gap device and showing cover layer deposition and channel formation after removal of excess active material, according to an exemplary embodiment of the present invention.

FIGS. 6A and 6B are cross-sectional views respectively taken along lines A-A and B-B from FIG. 6C, FIG. 6C is a top view and FIG. 6D is a three-dimensional view illustrating fabrication of a gap device and showing cover layer and channel formation after removal of excess active material, according to an exemplary embodiment of the present invention. Referring to FIGS. 6A-6D, after planarization as described in connection with FIG. 4, and prior to removal of the template structure as described in connection with FIG. 5, a cover layer 204, which can include the same or similar material to layer 104, but does not necessarily have to be the same material, is formed on the remaining portion of the active material layer 108 and template structure 106, as well as on dielectric layer 104. The cover layer 204 can be formed using deposition techniques, such as, for example, PVD, CVD, or ALD. Other methods may include direct bonding, ionic bonding, fusion bonding, or direct printing.

Channels are formed through openings 212a in the cover layer 204 over portions of the template structure 106. The openings 212a can be formed by an appropriate removal process, such as, for example, etching, to remove portions of the cover layer 204 to access the buried template structure 106. The channels, also referred to herein as gaps, are created by removal of the buried template 106.

The shape of the template structure 106 and the active material structure 108 shown in FIGS. 6C and 6D is an example, and the embodiments of the present invention are not necessarily limited thereto. For example, template structure 106 and the active material structure 108 illustrated in other figures may have a different shape than what is shown in FIGS. 6C and 6D.

Figure 7A:
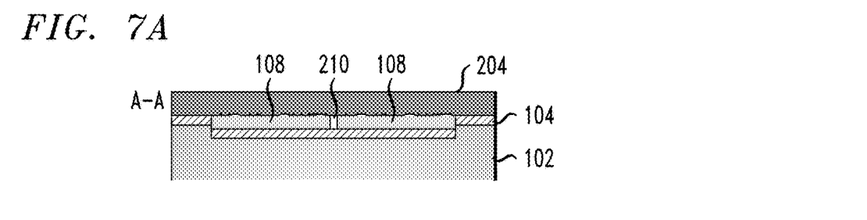
Figure 7B:
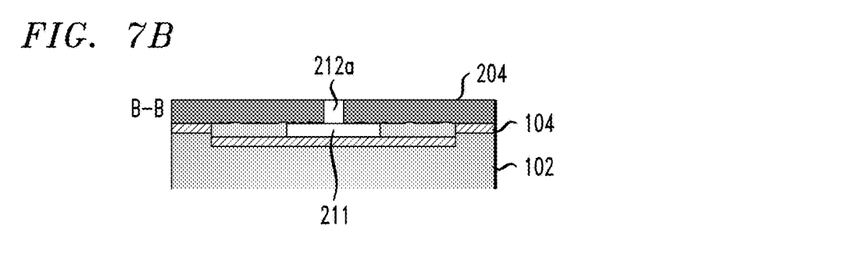
Figure 7C:
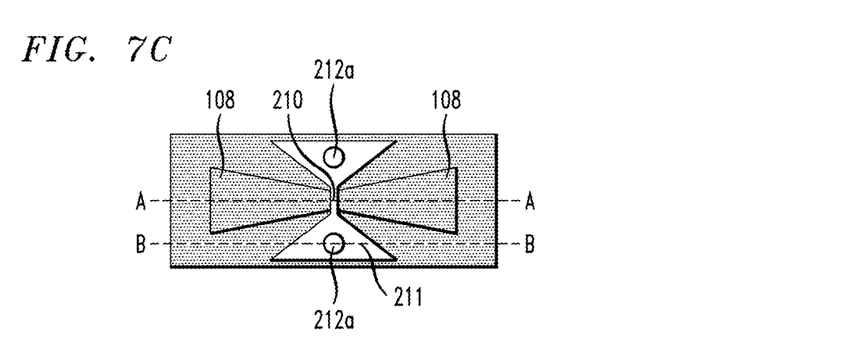
Figure 7D:
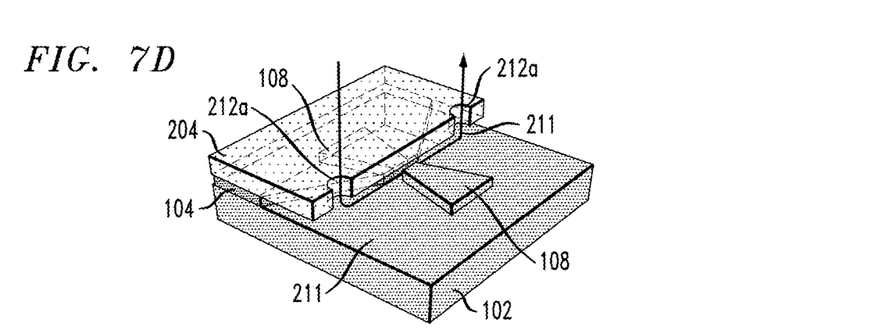
FIG. 7D is a three-dimensional view illustrating fabrication of a gap device and showing selective removal of a buried template through channels, according to an exemplary embodiment of the present invention.

FIGS. 7A and 7B are cross-sectional views respectively taken along lines A-A and B-B from FIG. 7C, FIG. 7C is a top view, and FIG. 7D is a three-dimensional view illustrating fabrication of a gap device and showing selective removal of a buried template through the openings 212a, according to an exemplary embodiment of the present invention. Referring to FIGS. 7B-7D, an etchant can pass through openings 212a, as shown by the arrow in FIG. 7D, to selectively remove the template structure 106, resulting in gaps 210 and 211 left by the removal of the template structure 106. As shown in FIG. 7A, the gap 210 is formed between opposing sections of the active material layer 108 in the space where a portion of the template structure 106 was embedded by the active material layer 108. Referring to FIG. 7B, another gap 211 is formed at a different portion where another portion of the template structure 106 was not embedded by the active material layer 108.

As can be understood in connection with FIGS. 6A-6D, and 7A-7D, in accordance with an embodiment of the present invention, an accurate alignment of a channel carrying an analyte-containing medium with a functional structure composed by the active material can be achieved. This can provide a required optimal interaction of analytes with a strong field enhancement present in the feed-gap of an optical or plasmonic antenna. If the antenna is to be functionalized with receptor molecules, the channel allows for receptor molecules to be placed just in the feed gap region for optimal binding and release. In case of electrical probing modalities, the active material can be a transistor or capacitor with high sensitivity in the electrical properties in respect to analytes in the channel.

In accordance with embodiments of the present invention, gaps of 5 nm or less exhibit theoretically proposed extreme field gradient conditions that are sufficiently large enough to change the optical selection rules in scattering processes, enabling detection of infrared modes in addition to Raman modes. Embodiments of the present invention may change molecular spectroscopy entirely as the structures resulting from the embodiments of the present invention make it possible to provide the most comprehensive information in a single experiment with single-molecule sensitivity. The extreme field gradient conditions enabled by the structures resulting from the embodiments of the present invention can be used in devices such as sensors with embedded nanochannels (e.g., channels created by removal of a template structure) for gaseous analyte detection. Such sensors can potentially be used for cancer-cell detection by breath analysis, or in other applications in molecular sensing, where self-aligned channels for gas or liquid media (e.g., channels created by removal of a template structure) are used for optimized interactions between high-field regions and an analyte-containing medium. Accordingly, analyte gas that is probed in a plasmonic structure can pass through the channels similar to an etchant as illustrated by the arrow FIG. 7D. In case of electrical functionality, the high electrical field can lead to ionization or field-dependent electro-chemical interactions, to be used to control synthetic step on the single-molecule level or as filtering and selection elements.

The process described in connection with FIGS. 1-5 can be used to create nanometer-sized waveguides, optical circuits and electro-optical modulators with excellent surface roughness due to treatment of the active material and narrow-gap distances. If applied for these applications, referring to FIGS. 8A, 8B, 8C, 8D, 9A, 9B, 9C, 9D, 10A, 10B, 10C and 10D, one or more buried template structures define the waveguides, and active non-linear optical material is deposited after selective removal of a template structure.

Figure 8A:
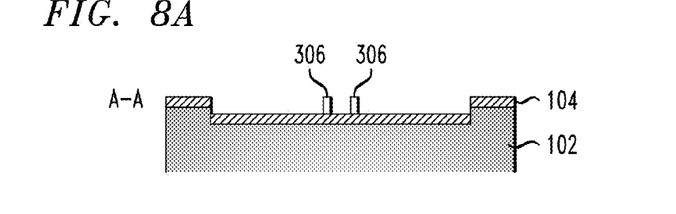
Figure 8B:
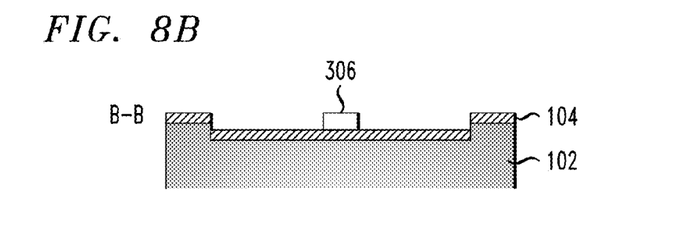
Figure 8C:
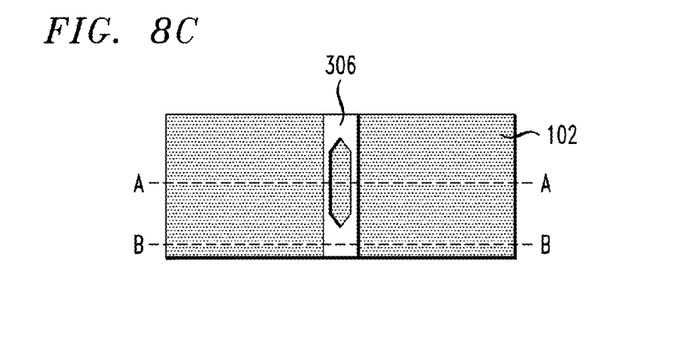
Figure 8D:
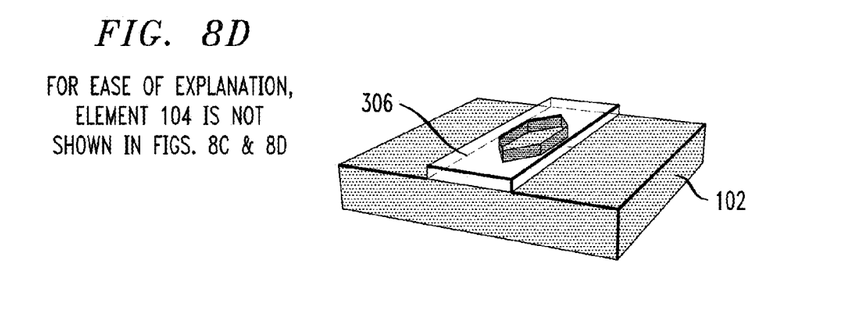
FIG. 8D is a three-dimensional view illustrating fabrication of a gap device and showing waveguide patterning using buried material, according to an exemplary embodiment of the present invention.
Figure 9A:
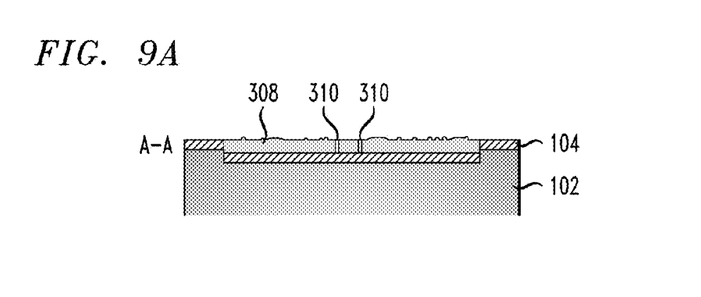
Figure 9B:
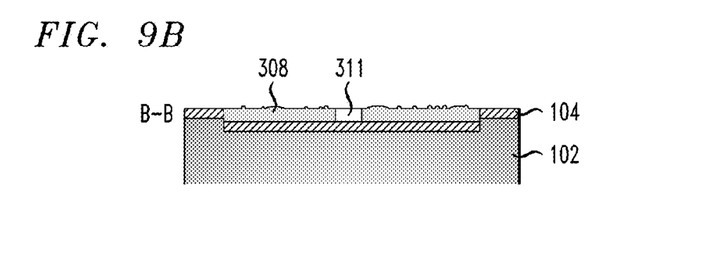
Figure 9C:
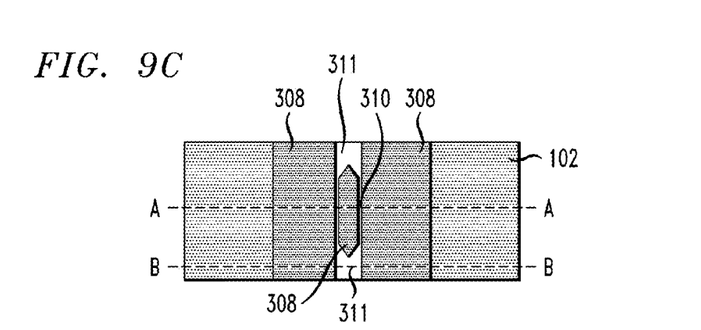
Figure 9D:
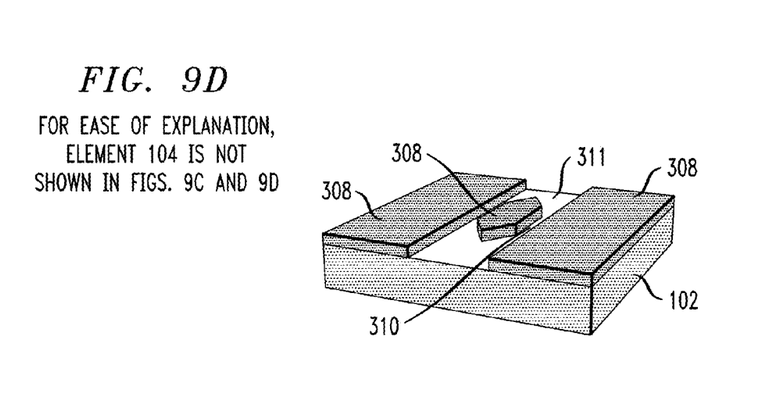
FIG. 9D is a three-dimensional view illustrating fabrication of a gap device and showing active material deposition, removal of excess active material and selective removal of buried material, according to an exemplary embodiment of the present invention.
Figure 10A:
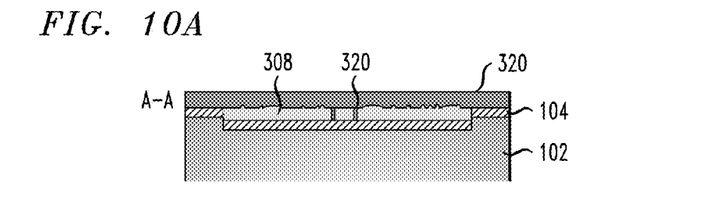
Figure 10B:
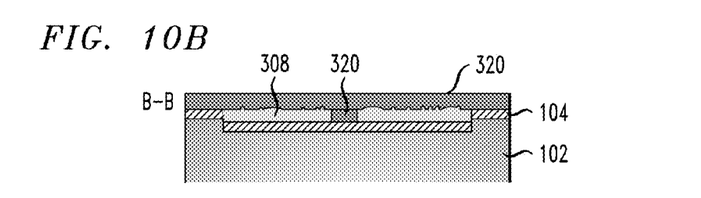
Figure 10C:
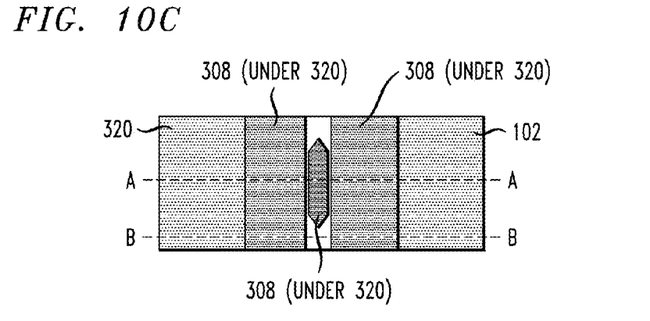
Figure 10D:
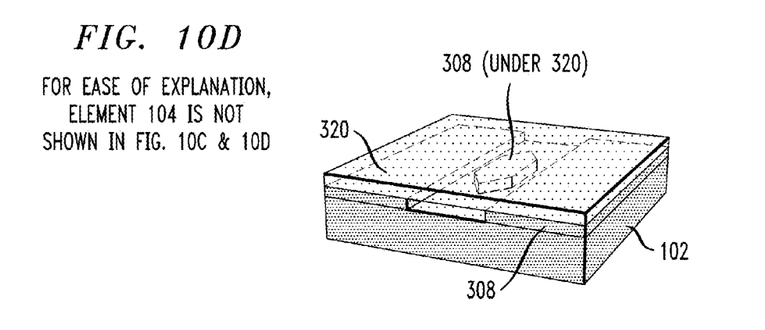
FIG. 10D is a three-dimensional view illustrating fabrication of a gap device and showing deposition of active non-linear optical material, according to an exemplary embodiment of the present invention.

Referring to FIGS. 8A and 8B, which are cross-sectional views respectively taken along lines A-A and B-B of the top view of FIG. 8C, waveguide and active-element patterning is performed using buried template structure 306 to define waveguides and circuits thereof. The template structure 306 can be formed using the same or similar processes as those described in connection with FIGS. 1 and 2. The shape of the template structure 306 shown in FIGS. 8C and 8D is an example, and the embodiments of the present invention are not necessarily limited thereto.

Referring to FIGS. 9A-9D, using the same or similar processing as described in connection with FIG. 3, an active material layer 308 is deposited to cover top and side surfaces of the template structure 306, and is formed on exposed portions of the dielectric layer 104. Then, using the same or similar processing as described in connection with FIG. 4, excess active material is removed. In addition, using the same or similar processing as described in connection with FIG. 5, the template structure 306 is selectively removed to create gaps 310 and 311. Depending on the configuration of the template structure 306 and the surrounding active material layer 308, gaps 310 and 311 can have different widths. As shown, gaps 310 are narrower than gaps 311.

Then, referring to FIGS. 10A-10D, active non-linear optical material 320 is deposited on the resulting structure. As can be seen, the active optical material layer 320 is deposited on the active material layer 308 and fills in the gaps 310 and 311 between sections of the active material layer 308 created by the removal of the template structure 306. The active optical material layer 320 can be deposited using deposition techniques, such as, for example, solution-based spin-coating, self-assembly, PVD, CVD or ALD.

As can be understood in connection with FIGS. 8A-10D, in accordance with an embodiment of the present invention, plasmonic waveguides can be made very narrow (e.g., less than 10 nm) and integration of active optical elements are feasible with self-alignment properties in respect to the connecting waveguides. As a result, ideal modulation properties in a Mach-Zehnder type of device can be achieved as the field gradient over the non-linear optical material is enhanced, which in return reduces the required driving voltages of the non-linear electro-optical effect for phase modulation. FIGS. 8-10 depict the formation of a Mach-Zehnder modulator embedded into the waveguide structure where the three segments composed of the active material have to be electrically driven for operation. Moreover, the optimal morphology achieved by the post-growth treatments or by employing directly monocrystalline materials (see, e.g. FIGS. 11, 12A and 12B below) can drastically reduce propagation and modulation losses by at least a factor of 200 based on propagation experiments of amorphous versus crystalline materials of gold (Au) and silver (Ag).

Figure 11:
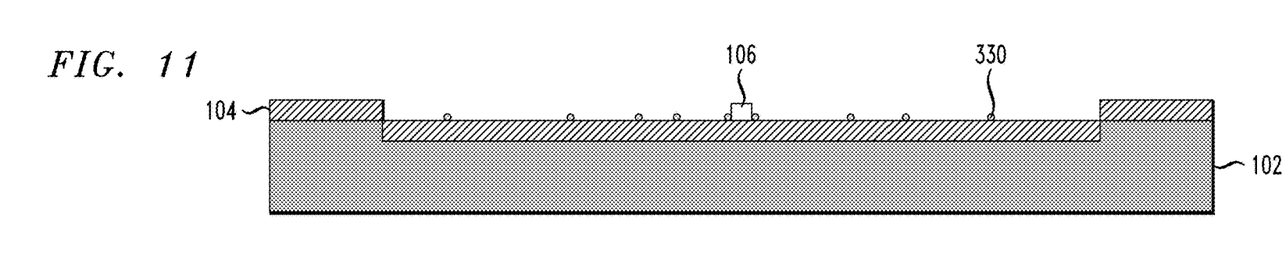
FIG. 11 is a cross-sectional view illustrating fabrication of a gap device and showing seed deposition, according to an exemplary embodiment of the present invention.
Figure 12A:
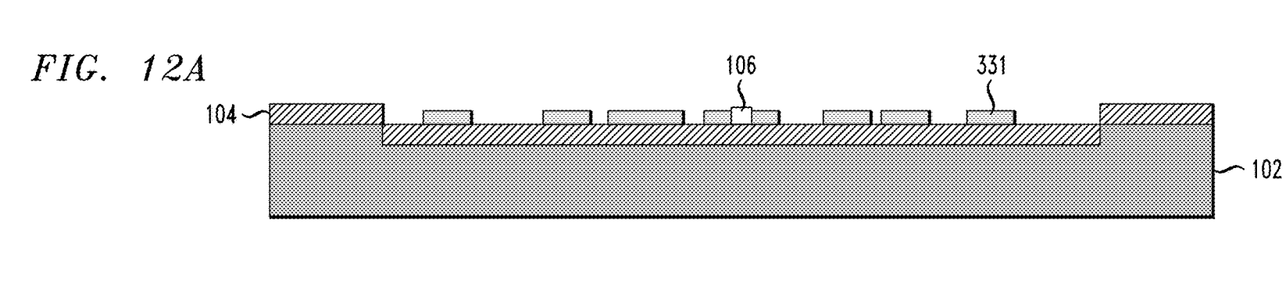
FIGS. 12A and 12B is a cross-sectional views illustrating fabrication of a gap device and showing seed-mediated or nucleation-induced growth of monocrystals, according to an exemplary embodiment of the present invention.
Figure 12B:
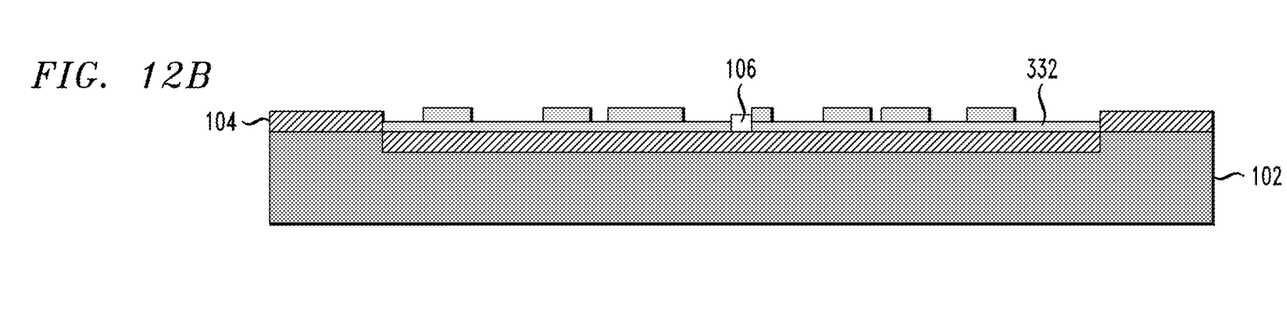

As mentioned herein, apart from reduced surface and line-edge roughness, material morphology is of similar importance for plasmonic devices. In this respect, monocrystalline or layer materials can be grown using, for example, seed mediated or nucleation growth to optimize material morphology. FIGS. 11, 12A and 12B illustrate how a buried template can be used as a spacer upon seed-mediated growth of monocrystalline materials, such as, for example, Au nanoplatelets. Referring to FIGS. 11, 12A and 12B, after formation of a template structure 106 as described in connection with FIGS. 1 and 2, seed particles 330 for growth of nanoplatelets (e.g., Au nanoplatelets) are deposited on portions of the dielectric layer 104, and around the template structure 106. Referring to FIGS. 12A and 12B, seed mediated growth occurs to result in larger sections 331 until monocrystal sections 332 are formed on opposite (e.g., left and right) sides of a template structure 106, which functions as a spacer.

Figure 13:
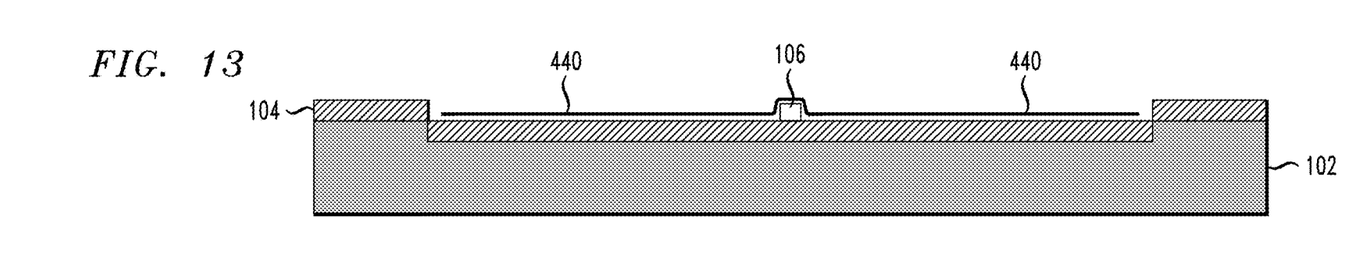
FIG. 13 is a cross-sectional view illustrating fabrication of a gap device and showing deposition of two-dimensional layered material on a buried template, according to an exemplary embodiment of the present invention.
Figure 14:
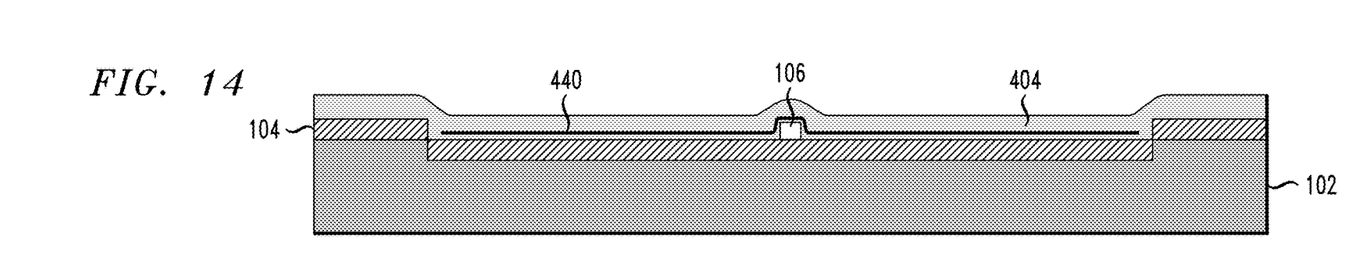
FIG. 14 is a cross-sectional view illustrating fabrication of a gap device and showing deposition of an embedding layer, according to an exemplary embodiment of the present invention.
Figure 15:
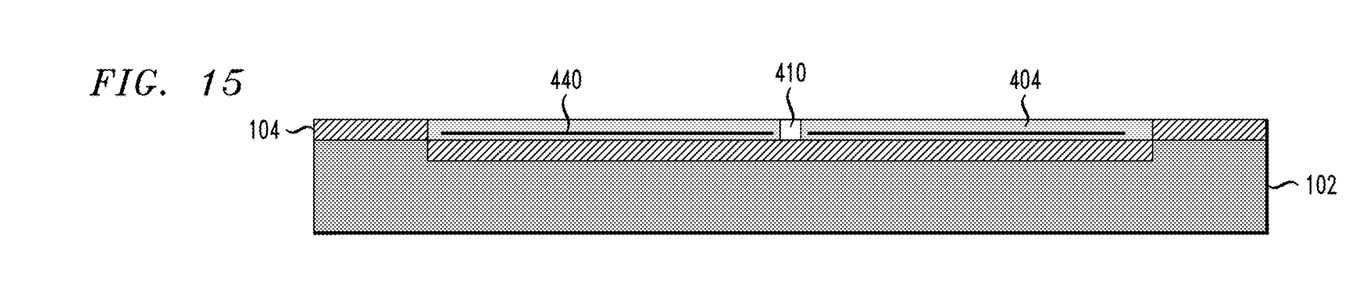
FIG. 15 is a cross-sectional view illustrating fabrication of a gap device and showing removal of excess portions of the embedding layer, and selective removal of the buried template, according to an exemplary embodiment of the present invention.

The embodiments of the present invention also can include patterning a 2D-layered material by depositing the 2D-layered material as the active material layer on top of a buried template (e.g. by solution-based deposition, printing, and/or direct growth), embedding the 2D-layered material with a passive material (e.g. an oxide) and using the same or similar planarization steps (e.g., CMP) and release steps as described in connection with FIGS. 4 and 5. FIGS. 13-15 illustrate how 2D-layered materials, such as, but not necessarily limited to, graphene, can be integrated into a gap device.

FIG. 13 is a cross-sectional view illustrating fabrication of a gap device and showing deposition of two-dimensional layered material on a buried template, according to an exemplary embodiment of the present invention. Referring to FIG. 13, after formation of a template structure 106 as described in connection with FIGS. 1 and 2, a 2D-layered material 440 is deposited to cover top and side surfaces of the template structure 106, and on some of the exposed portions of the dielectric layer 104. As noted above, solution-based deposition, printing, and/or direct growth can be used to deposit the 2D-layered material 440. Then, referring to FIG. 14, the 2D-layered material 440 is embedded by the deposition of an embedding layer 404, which can include the same or similar material to the dielectric layer 104, but does not necessarily have to be a dielectric layer. The embedding layer 404 is formed to embed the 2D-layered material 440 and template structure 106, and is formed on the exposed portions of the dielectric layer 104. The embedding layer 404 can be formed using deposition techniques, such as, for example, PVD, CVD or ALD. Other methods may include direct bonding, ionic bonding, fusion bonding, or direct printing.

Referring to FIG. 15, using the same or similar processing as described in connection with FIG. 4, excess portions of the embedding layer 404 and 2D-layered material 440 are removed. Then, using the same or similar processing as described in connection with FIG. 5, the template structure 106 is selectively removed. As shown in FIG. 15, a gap 410 is formed in the space previously occupied by the template structure 106 between opposing sections of the embedding layer 404 with the 2D-layered material 440 embedded therein.

Embodiments of the present invention provide processes to fabricate plasmonic structures having sub-10 nm feature sizes, and lowered surface and line-edge roughness, while drastically reducing losses due to improved material morphology. Embodiments of the present invention also allow monocrystalline materials to be utilized, which can be desirable for plasmonic applications.

Resulting structures of embodiments of the present invention include, but are not necessarily limited to, plasmonic and plasmonic-photonic waveguides and circuits, channels for hybrid photonic-plasmonic modulators, trenches for sensing, and channels for sensing. Applications of embodiments of the present invention include, but are not necessarily limited to sensing of different compounds with ultra-low volumes and single-molecule sensitivity with applications in security, environment, health, medical or biological sectors, waveguides at semiconductor device level length scales, optical components, such as modulators at subwavelength optical scales, and electronic applications, such as memory applications, where ultra-narrow gaps are filled with memory or transistor materials.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

We claim:

1. A method for manufacturing a gap device, comprising:
   forming a template structure on a substrate;
   depositing an active material layer on the substrate and on the template structure, wherein the active material layer covers at least top and side surfaces of the template structure;
   planarizing the active material layer;
   depositing a cover layer on the active material layer and the template structure after the planarization;
   forming one or more openings through the cover layer which provide access to the template structure; and
   selectively removing the template structure with respect to the active material layer and the substrate to create a gap in the active material layer corresponding to the width of the template structure;
   wherein the selective removal of the template structure is performed through the one or more openings;
   wherein the gap is embedded within the active material layer, and at least a portion of the gap is overlapped by the cover layer; and
   wherein the cover layer closes off at least part of an open top region of the gap while the gap remains unfilled.

2. The method according to claim 1, further comprising selectively removing a portion of the template structure to reduce the template structure to a second dimension smaller than a first dimension of the template structure, wherein the active material layer is deposited on the reduced template structure.

3. The method according to claim 1, wherein the planarization removes portions of the active material layer down to or below the top surface of the template structure, leaving a portion of the template structure on the substrate embedded in the active material layer.

4. The method according to claim 1, wherein the planarization separates the active material layer into a first portion on a first side of the template structure, and a second portion on a second side of the template structure opposite the first side.

5. The method according to claim 1, further comprising patterning the template structure using at least one of photolithography, electron-beam lithography, probe-based lithography, and imprint lithography.

6. The method according to claim 1, wherein the formation of the template structure is performed using at least one of deposition and assembly.

7. The method according to claim 2, wherein the selective removal of the portion of the template structure is performed using at least one of oxidation and etching.

8. The method according to claim 2, wherein the selective removal of the portion of the template structure is performed using a process that is at least one of self-limiting and cycleable.

9. The method according to claim 1, further comprising treating the template structure to reduce at least one of line-edge roughness and surface roughness of the template structure.

10. The method according to claim 1, further comprising treating the active material layer to improve at least one of material morphology of the active material and interfacial quality between the active material layer and the template structure.

11. The method according to claim 1, wherein a width of the template structure is in the range of about 1 nanometer to about 2 micrometers.

12. The method according to claim 2, wherein the second dimension is a width of the reduced template structure and is less than about 10 nanometers.

13. The method according to claim 1, wherein planarizing the active material layer is performed using a process that is at least one of chemical-mechanical polishing, mechanical polishing and etching.

14. A method for manufacturing a gap device, comprising:
forming a template structure on a substrate;
patterning the template structure to a critical dimension;
removing a portion of the template structure to reduce the template structure to a second dimension less than the critical dimension;
depositing an active material layer on the substrate and on the reduced template structure, wherein the active material layer covers at least a portion of side surfaces of the reduced template structure;
removing excess portions of the active material layer;
depositing a cover layer on the active material layer and the reduced template structure after the removing of the excess portions of the active material layer;
forming one or more openings through the cover layer which provide access to the reduced template structure; and
selectively removing the reduced template structure with respect to the active material layer to create a gap in the active material layer corresponding to the width of the reduced template structure;
wherein the selective removal of the template structure is performed through the one or more openings;
wherein the gap is embedded within the active material layer, and at least a portion of the gap is overlapped by the cover layer; and
wherein the cover layer closes off at least part of an open top region of the gap while the gap remains unfilled.

15. The method according to claim 14, wherein the formation of the active material layer is performed using at least one of seed-mediated growth, nucleation-induced growth and chemical vapor deposition.

16. A method for manufacturing a gap device, comprising:
forming a template structure on a substrate;
reducing the template structure to a width less than about 10 nanometers;
depositing an active material layer on the substrate and at least on top and side surfaces of the template structure;
removing excess portions of the active material layer to expose the top surface of the template structure;
depositing a cover layer on the active material layer and the template structure after the removing of the excess portions of the active material layer;
forming one or more openings through the cover layer which provide access to the template structure; and
selectively removing the template structure with respect to the active material layer and the substrate to create a gap in the active material layer corresponding to the width of the template structure,
wherein the selective removal of the template structure is performed through the one or more openings;
wherein the gap is embedded within the active material layer, and at least a portion of the gap is overlapped by the cover layer; and
wherein the cover layer closes off at least part of an open top region of the gap while the gap remains unfilled.

* * * * *